United States Patent [19]

Speck

[11] Patent Number: 4,870,061

[45] Date of Patent: Sep. 26, 1989

[54] USE OF N-ACETYLGLUCOSAMINE FOR THE THERAPY OF DEGENERATIVE JOINT DISEASE AND RELATED DISEASES

[76] Inventor: Ulrich Speck, Benediktinerstrasse 50, D-1000 Berlin 28, Fed. Rep. of Germany

[21] Appl. No.: 302,403

[22] Filed: Jan. 26, 1989

Related U.S. Application Data

[63] Continuation-in-part of Ser. No. 1,008, Jan. 7, 1987, abandoned.

[30] Foreign Application Priority Data

Jan. 29, 1986 [DE] Fed. Rep. of Germany ....... 3602670

[51] Int. Cl.$^4$ ............................................. A61K 27/00
[52] U.S. Cl. ..................... 514/62; 514/825; 536/55.2
[58] Field of Search .................. 514/62, 825; 536/55.2

[56] References Cited

U.S. PATENT DOCUMENTS

| | | | |
|---|---|---|---|
| 2,538,106 | 1/1951 | Kuehl | 536/55.2 |
| 2,802,819 | 8/1957 | Lederer et al. | 536/55.2 |
| 3,118,875 | 1/1964 | Adams | 536/55.2 |
| 3,683,076 | 8/1972 | Rovati | 514/62 |
| 3,697,652 | 10/1972 | Rovati et al. | 536/55.2 |
| 4,006,224 | 2/1977 | Prudden | 514/62 |
| 4,181,740 | 1/1980 | Zumin et al. | 536/55.2 |
| 4,216,208 | 8/1980 | De Barbieri | 514/62 |
| 4,267,313 | 5/1981 | Sannan et al. | 536/55.2 |
| 4,438,117 | 3/1984 | Cherkofsky | 514/825 |
| 4,590,067 | 5/1986 | Meisner | 424/54 |
| 4,607,025 | 8/1986 | Petitou et al. | 536/55.2 |
| 4,647,453 | 3/1987 | Meisner | 514/62 |

FOREIGN PATENT DOCUMENTS

| | | | |
|---|---|---|---|
| 3445324 | 6/1986 | Fed. Rep. of Germany | 514/62 |
| 46-24380 | 7/1971 | Japan | 514/62 |
| 896940 | 5/1962 | United Kingdom | 514/62 |

*Primary Examiner*—Ronald W. Griffin
*Attorney, Agent, or Firm*—Bierman and Muserlian

[57] ABSTRACT

The invention refers to the use of N-acetylglucosamine for the therapy of degenerative diseases of the joints and of the connective and the supporting tissues as well as for the therapy of related diseases, wherein the N-acetylglucosamine is administered to the body through buccal absorption.

7 Claims, 2 Drawing Sheets

USE OF N-ACETYLGLUCOSAMINE FOR THE THERAPY OF DEGENERATIVE JOINT DISEASE AND RELATED DISEASES

CROSS-REFERENCE TO RELATED APPLICATION

This application is a continuation-in-part of U.S. application Ser. No. 07/001,008, filed Jan. 7, 1987, now abandoned.

BACKGROUND AND SUMMARY OF THE INVENTION

The present invention refers to the use of N-acetyl-glucosamine for the therapy of degenerative diseases of the joints and of the connective and the supporting tissues as well as for the therapy of related diseases. Moreover, the invention comprises the use of N-acetyl-glucosamine for the production of drugs for corresponding therapies.

Degenerative diseases of the joints (arthrosis) are widespread with human beings as well as with animals of middle and higher age. They are a frequent reason for poor general condition and limited ability to work. One main reason for these diseases is the destruction of glucosaminoglycanes (GAG) which are an essential component of the cartilage substances and of other flexible elements as well as a contributor to the lubrication of the joints.

The therapy of these painful, partly inflammatory conditions often only takes place symptomatically with the aid of non-steroidal anti-inflammatory drugs such as, for instance, indomethacin, or even corticoids. Both groups of therapeuticals cause severe side effects and should therefore be used as little as possible. Moreover, the application of non-steroidal anti-inflammatory drugs and corticoids entails the danger of further shifting the metabolism of the GAGs in the direction of accelerated degradation. Thus, the advantages of momentary relief of the symptoms of the disease, such as pain and immobility of the joints, is—besides other risks—connected with the danger of an acceleration in the degenerative processes which cause the underlying disease.

It is well-knwon that in contrast to the above, glucosaminoglycanes or a precursor of GAGs, glucosamine, exert a causal therapeutical effect. That effect is, on the one hand, based upon the incorporation of the corresponding elements in to the GAGs and, on the other hand, on the stimulation of the new synthesis of GAGs caused by an increase in the concentration of precursors of their synthesis. An inhibition of the enzymatic decomposition processes is also assumed. Thus, there exists the possibility to favorably influence the metabolic processes being causal for the disease, and to thereby contribute to the healing or at least to the retardation of the degenerative processes being the origin of the disease.

Drugs available for the last-mentioned causal therapy, however, are also not yet ideal. GAGs, being isolated from biological material, have the disadvantage of being complex natural products: It is hardly possible, or at least extremely difficult, to define them clearly and their parenteral application is necessary for guaranteeing a sufficient bio-availability. Moreover, there always exists the risk of anaphylactical reactions. The limited solubility and the high viscosity of concentrated solutions make it even more difficult to administer them with the desired high dosage.

Instead of the natural GAGs, glucosamine sulfate has also been administered orally, intramuscularly and intraarticularly with good therapeutical effect. Glucosamine sulfate has the great advantage of being a clearly definable compound with respect to identity, purity and stability. Glucosamine sulfate, as a low-molecular natural substance, does not cause any allergies and hardly gives reason to expect toxic effects in case of the necessary dosage. On the other hand, glucosamine sulfate has an essential disadvantage, as can for instance be taken from the prescribing information Dona ®200-S of Opfermann-Arzneimittel, 5060 Bergisch-Gladbach.

The oral form of glucosamine is obviously much less effective than the intravenous or intramuscular injection. A weekly oral dosage of 5,250 mg is recommended, while, parenterally, only 1,200 mg are necessary. The physiological pH-value of the more efficient injection preparation, however, is not sufficiently stable in solution. Thus, it is prepared, stored and delivered with an acidic pH-value, and has to be neutralized by the physician before use. For this purpose, a buffer is added to the glucosamine sulfate solution. Glucosamine sulfate solution and buffer as a whole have, in case of the necessary dosage and concentration, such a high osmolality relative to the blood that lidocaine has to be added as a local anaesthetic. Only by means of that additive can the pain caused by the injection into the joints by sufficiently reduced. Thus, the glucosamine sulfate, although not toxic as such, is combined with the side effects of the lidocaine (ECG and other circlatory disturbances, vertigo, vomiting).

Other preparations, as described in the recently published application EP 85 112 913.0, comprise complex mixtures of individual components showing quite a number of obvious disadvantages:

(a) The chemical stability of every element in the mixture is difficult to obtain, particularly under long-term storage conditions.

(b) The Health Authorities of many countries, for good reasons, behave very restrictively as far as the approval of combined preparations is concerned. Thus, evidence is required that every component is effective, and often in addition that the fixed combination of the individual components has specific advantages. Both types of evidence can hardly be given for combinations comprising more than two ingredients.

It is therefore an object of the present invention to overcome the above-mentioned disadvantages and to make available an agent with only one active principle for use in the therapy of degenerative diseases of the joints and of the connective and the supporting tissues, as well as for the therapy of related diseases, which agent administered as such, delays or prevents the progression of the disease, or starts the healing process.

DETAILED DESCRIPTION OF THE INVENTION

Figure 1:
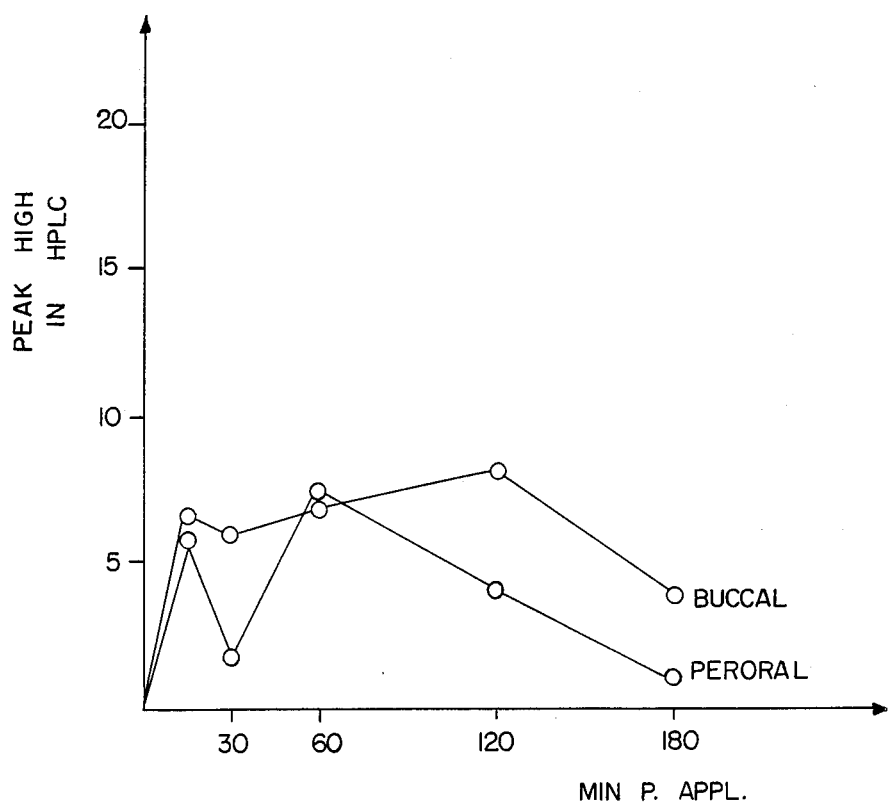
FIG. 1 graphically compares the absorption following intragastral (peroral) and buccal administration of 2 ml of an aqueous solution of 20 mg of N-acetylglucosamine.

According to the present invention, the above-described problems are solved by using a buccal administration of N-acetylglucosamine for the therapy mentioned above.

Surprisingly, Applicant has found that N-acetylglucosamine is best suited for applications relying upon buccal absorption. Whereas the taste of glucosamine is unacceptable for patients, N-acetylglucosamine is slightly sweet without any bitter taste. Further, while N-acetylglucosamine is neither a small molecule nor lipophilic, Applicant has discovered that surprisingly, it is well and rapidly absorbed by buccal mucosa.

Preferred embodiments of the invention are mentioned in the sub-claims.

It has been surprisingly realized that glucosamine can be replaced by N-acetylglucosamine. In order to be integrated into the GAGs, both substances first have to be phosphorylated.

Until now, it has been believed that N-acetylglucosamine as a precursor for the synthesis of proteoglycanes does not play any or at most, only an insignificant role in the mammalian organism; see Vidal y Plana, R. R. and K. Karzel: Glucosamin, Seine Bedeutung für den Knorpelstoffwechsel der Gelenke; 1. Biochemie der Proteoglycane, Untersuchungen an in-vitro Kulturen embryonaler Mäuse-Fibroplasten and Knochenanlagen, Fortschr. Med. 98, 555–594, 1980.

N-acetylglucosamine when compared to glucosamine and its salts, for instance the sulfate, shows essential advantages:

(a) Better stability in aqueous solution.
(b) A lower osmolality of the equimolar solution because of the lack of ionic characteristics (no anion for the neutralization) and the absence of a buffer for adaptation of the pH-value.
(c) No necessity to add a local anaesthetic.
(d) Clearly better compatibility in case of parenteral application.
(e) At least equal, obviously even better incorporation into the glucosaminoglycanes of the joints after administration of N-acetylglucosamine than after administration of glucosamine salts. Comparative figures are shown in Table 1.

Additional tests have meanwhile confirmed that N-acetylglucosamine, particularly after oral and most preferably after buccal administration as desired for the therapy, is used for the synthesis of the joint cartilages in an amount at least three times higher than glucosamine.

The present invention further refers to the use of N-acetylglucosamine for the production of drugs for the therapy of degenerative diseases of the joints and of the connective and supporting tissues as well as for the therapy of related diseases.

N-acetylglucosamine as such or in combination with usual excipients can be prepared as a solution for the intraarticular, intravenous, intramuscular or other injection or infusion, or for oral or buccal application. N-acetylglucosamine is appropriate for buccal administration as powder or granules because of its pleasant taste. It can also be filled into capsules for the exact dosage together with or without excipients, or can be prepared as tablets, coated tablets or lozenges. Since N-acetylglucosamine is chemically stable and relatively inert, preparations can be prepared in combination with many other drugs, without entailing a loss of effectiveness of one of the ingredients.

TESTS

About 10 $\mu$Ci N-acetyl-$^{14}$C-glucosamine or $^3$H-glucosamine were administered to mice either intramuscularly or orally, three times at an interval of six hours. About 24 hours after the (last) application, the animals were sacrificed and the introduction of the marked substances into the GAGs of the joints of the rear extremities was determined.

TABLE 1

Introduction of glucosamine and N—acetylglucosamine into the glucosaminoglycanes of the joints of a mouse.

| Substance | Way of Application | Dosage ($\mu$mole) | nmoles in the GAGs of an extremity |
|---|---|---|---|
| glucosamine | 3 × p.o. | 1.7 | 0.013 |
|  |  |  | 0.0099 |
|  |  |  | 0.018 |
|  |  |  | 0.019 |
| N—acetyl-glucosamine | 3 × p.o. | 1.8 | 0.039 |
|  |  |  | 0.041 |
|  |  |  | 0.047 |
|  |  |  | 0.047 |
| glucosamine | i.m. | 0.88 | 0.033 |
|  |  |  | 0.013 |
|  |  |  | 0.089 |
|  |  |  | 0.052 |
| N—acetyl-glucosamine | i.m. | 0.85 | 0.12 |
|  |  |  | 0.094 |
|  |  |  | 0.22 |
|  |  |  | 0.21 |

To demonstrate the substance's surprising buccal absorption rate, tests were conducted using the methodology set forth in studies on drug absorption from oral cavity; physicochemical factors affecting absorption from hamster cheek-pouch; Kurosaki Y., Aya N., Okada Y., Nakayama T., Kimura T., J. Pharmacobio-Dyn. 9,3: 287–296 (1986). Male hamsters were anesthetized and N-acetylglucosamine dissolved in 2 ml of water was inserted into the cheek pouch or into the stomach. The animals were sacrificed at various times after the administration, and the plasma was deproteinized by the addition of an equal volume of methanol. HPLC-separation (Shimadzu LC-6A) was performed on a Si-100-column (Serva) using 0.1 ml of methanol. The mobile phase consisted of a mixture of acetonitrile in acetic acid, 9:1 (v/v); quantified by refractometry.

Aqueous solutions of N-acetylglucosamine having a concentration of 5 to 55 mg/ml and a volume of about 0.5 to 1,000 ml, are appropriate for the injection or the infusion. Optionally, the osmolality of the solutions (below about 60 mg N-acetylglucosamine/ml) has to be adapted to the physiological osmotic pressure by addition of for instance NaCl or glucose. The total dosage preferably is between 100 and 5,000 mg N-acetylglucosamine. In case of oral administration, the preferred dosage is between 500 mg and 5,000 mg/day.

By using N-acetylglucosamine, it has for the first time become possible to offer the necessary form of injection for an effective arthrosis therapy as a well compatible preparation stable over a long period and applicable in an uncomplicated way, without undesired additives. N-acetylglucosamine is better tolerated than glucosamine sulfate and is unexpectedly incorporated into the glucosaminoglycanes of the joints at a higher rate.

Figure 2:
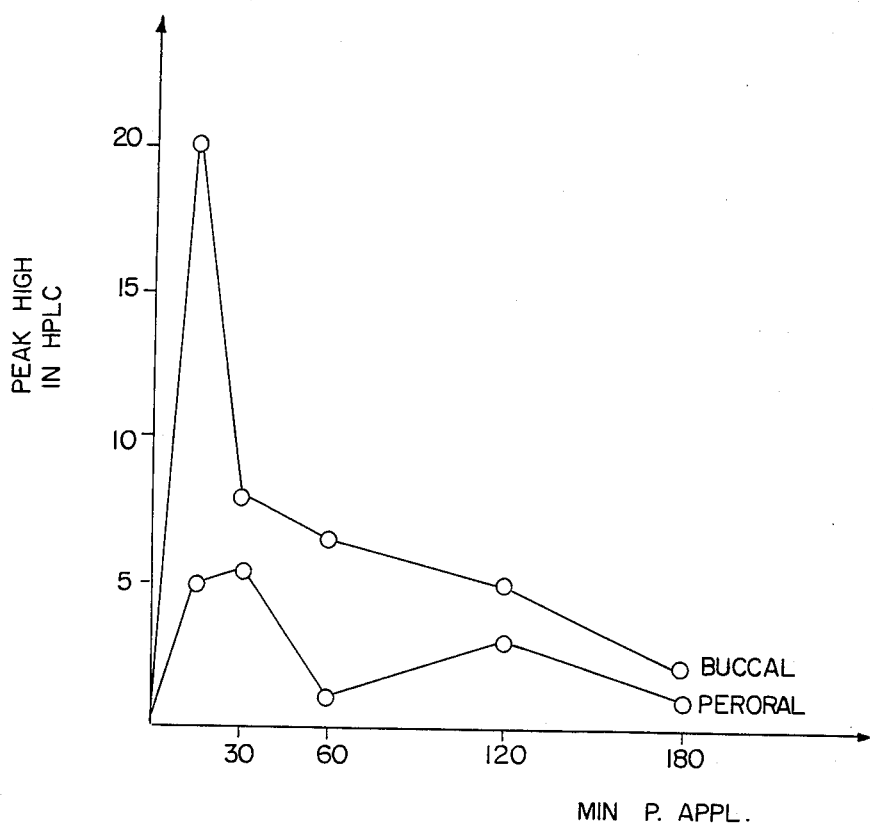
FIG. 2 graphically compares the absorption following intragastral (peroral) and buccal administration of 2 ml of an aqueous solution of 200 mg N-acetylglucosamine.

The results, illustrated in FIGS. 1 and 2 surprisingly indicate the buccal absorption of N-acetylglucosamine occurs in spite of the unfavorable physicochemical properties of the molecule. Plasma levels were higher and significantly more consistent after buccal administration than after conventional oral application. The areas under the drug concentration curves are clearly larger. The graphs demonstrate that buccal applications of N-acetylglucosamine result in high and reliable plasma levels and therefore, high efficacy as compared to oral administration.

EXAMPLES

1. Solution for the intravenous, intramuscular or intraarticular injection.

400 g N-acetylglucosamine p.a. are solved in 3,000 ml aqua pro injectione. The solution is filtered in a sterile way and filled vials in 3 ml portions. The vials are closed by fusing, and sterilized for 20 minutes at 121° C. The contents of active agent lies at >98%, the pH-value of the completely unbuffered solution of 6.3

2. Solution for the infusion.

6,000 g N-acetylglucosamine and 1,800 g NaCl p.a. are solved in 300 ml aqua pro injectione. The solution is filtered in a sterile way and filled into 50 ml infusion bottles. The bottles are autoclaved for 20 minutes at 121° C.

3. Tablets.

2,500 g N-acetylglucosamine are homogenously mixed in 1,000 g tablettose and 15 g magnesium stearate, then granulated and pressed into tablets.

Weight of one tablet: 351.5 mg.

Contents of N-acetylglucosamine per tablet: 250 mg.

The preferred drug preparations according to the present invention are those which release the active ingredient in the mouth, do not contain large amounts of additives (in order to avoid any undesirable dilution of the active ingredient), and do not display an unpleasant taste or consistency. Examples of preferred preparations are powders, granules, or solid drug forms which are slowly but completely dissolved in the mouth, such as a lozenge. A preferred dosage of the drug in warm bodies mammals in between 1.5 and 70 mg/kg of body weight. The most preferred dosage range is between 3.0 and 20 mg/kg.

I claim:

1. A method of treating degenerative diseases of the joints and connective and supporting tissues thereof in humans or warm blooded animals comprising administering buccally to humans or warm blooded animals an amount of N-acetylglucosamine sufficient to treat degenerative diseases of the joints and connective and supporting tissue of said humans or animals.

2. The method of claim 1 wherein said N-acetylglucosamine is administered in a dosage of between 1.5 and 70 mg/kg body weight of the humans or animals.

3. The method of claim 2 wherein said dosage is between 3.0 and 20 mg/kg.

4. The method of claim 1 wherein said N-acetylglucosamine is orally introduced as powder.

5. The method of claim 1 wherein said N-acetylglucosamine is orally introduced as granule.

6. The method of claim 1 wherein said N-acetylglucosamine is orally introduced as a lozenge.

7. The method of claim 1 wherein said N-acetylglucosamine is orally introduced into a cheek pouch as a solution.

* * * * *